United States Patent
Allred et al.

(10) Patent No.: US 7,274,771 B2
(45) Date of Patent: Sep. 25, 2007

(54) METHODS AND SYSTEMS FOR CONTROLLING EXPOSURE FOR MEDICAL IMAGING DEVICES

(75) Inventors: J. Joseph Allred, Centerville, UT (US); Steven E. Curtis, Salt Lake City, UT (US); Dimitri Yatsenko, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/120,448

(22) Filed: May 3, 2005

(65) Prior Publication Data

US 2006/0251216 A1    Nov. 9, 2006

(51) Int. Cl.
*H05G 1/64* (2006.01)
*H05G 1/44* (2006.01)
*H05G 1/42* (2006.01)

(52) U.S. Cl. .............. 378/98.12; 378/108; 378/97

(58) Field of Classification Search ............ 378/97, 378/98.7–114, 98.12, 108; 382/132; 250/370.09
See application file for complete search history.

(56) References Cited

U.S. PATENT DOCUMENTS

| | | | |
|---|---|---|---|
| 2,627,035 A * | 1/1953 | Bail | 378/110 |
| 4,797,905 A * | 1/1989 | Ochmann et al. | 378/108 |
| 5,617,462 A * | 4/1997 | Spratt | 378/98.7 |
| 6,151,454 A | 11/2000 | Pittman, Jr. | |
| 6,330,302 B1 * | 12/2001 | Joosten | 378/98.12 |
| 6,570,613 B1 | 5/2003 | Howell | |
| 6,766,064 B1 * | 7/2004 | Langan et al. | 382/274 |
| 2003/0016791 A1 * | 1/2003 | Ukita | 378/210 |
| 2006/0104496 A1 | 5/2006 | Arenson et al. | |

FOREIGN PATENT DOCUMENTS

WO    WO 00/38417 A1    6/2000
WO    WO 2005/093663 A1    10/2005

OTHER PUBLICATIONS

A. Ardeshir Goshtasby, "High Dynamic Range Reduction Via Maximization of Image Information," Department of Computer Science and Engineering, Wright State University, Dayton, OH 45435. E-mail: ardeshir@cs.wright.edu, 21 pgs.

* cited by examiner

*Primary Examiner*—Edward J. Glick
*Assistant Examiner*—Irakli Kiknadze
(74) *Attorney, Agent, or Firm*—The Small Patent Law Group; Dean D. Small

(57) ABSTRACT

Methods and systems for controlling exposure for medical imaging devices is provided. The method includes varying the exposure level of X-rays within an X-ray imaging system to generate a plurality of images having different exposure levels and combining the plurality of images in an additive process to form a single X-ray image.

20 Claims, 4 Drawing Sheets

METHODS AND SYSTEMS FOR CONTROLLING EXPOSURE FOR MEDICAL IMAGING DEVICES

BACKGROUND OF THE INVENTION

This invention relates generally to medical imaging systems and, more particularly, to methods and systems for controlling exposure of images in X-ray imaging devices.

The dynamic range of image processing, particularly in X-ray medical imaging systems, has increased, resulting in improved imaging. High dynamic range images and still single images are needed for three-dimensional (3D) image processing that use improved dynamic range processing software and hardware. The images processed by the improved dynamic range processing software and hardware are limited by the dynamic range of the image sensors. Consequently, imaging sensors having improved dynamic ranges are needed to provide these high dynamic range images. As a result, and partly based on medical need and market drive for the needed dynamic range improvement, solid state detectors have been developed for providing this higher dynamic range. However, solid state detectors are much higher in cost.

Many X-ray systems use lower cost image sensors, such as image intensifiers to convert X-rays to camera inputs. These lower cost image sensors, however, limit the dynamic range of the images produced. Thus, using these lower cost image sensors, reconstructed images are not provided at a higher dynamic range because of the limited dynamic range of the image sensors, such as image intensifiers. Therefore, the uses and applications of these image sensors are limited.

BRIEF DESCRIPTION OF THE INVENTION

In one exemplary embodiment, a method for controlling an X-ray imaging system is provided. The method includes varying the exposure level of X-rays within an X-ray imaging system to generate a plurality of images having different exposure levels and combining the plurality of images in an additive process to form a single X-ray image.

In another exemplary embodiment, an X-ray system is provided. The X-ray imaging system includes an X-ray imaging device for acquiring X-ray images and a controller for controlling the exposure level of a plurality of images acquired at each position of the X-ray imaging device. The X-ray imaging system further includes a processor for processing a plurality of acquired images in order to combine in an additive process the plurality of acquired images to generate a single X-ray image, with each acquired image having a different exposure level.

DETAILED DESCRIPTION OF THE INVENTION

Exemplary embodiments of systems and methods for controlling exposure for medical imaging systems, and in particular, X-ray imaging systems, are described in detail below. A detailed description of exemplary medical imaging systems, and specifically X-ray imaging systems will first be provided followed by a detailed description of various embodiments of methods and systems for controlling exposure of X-ray imaging systems.

Figure 1:
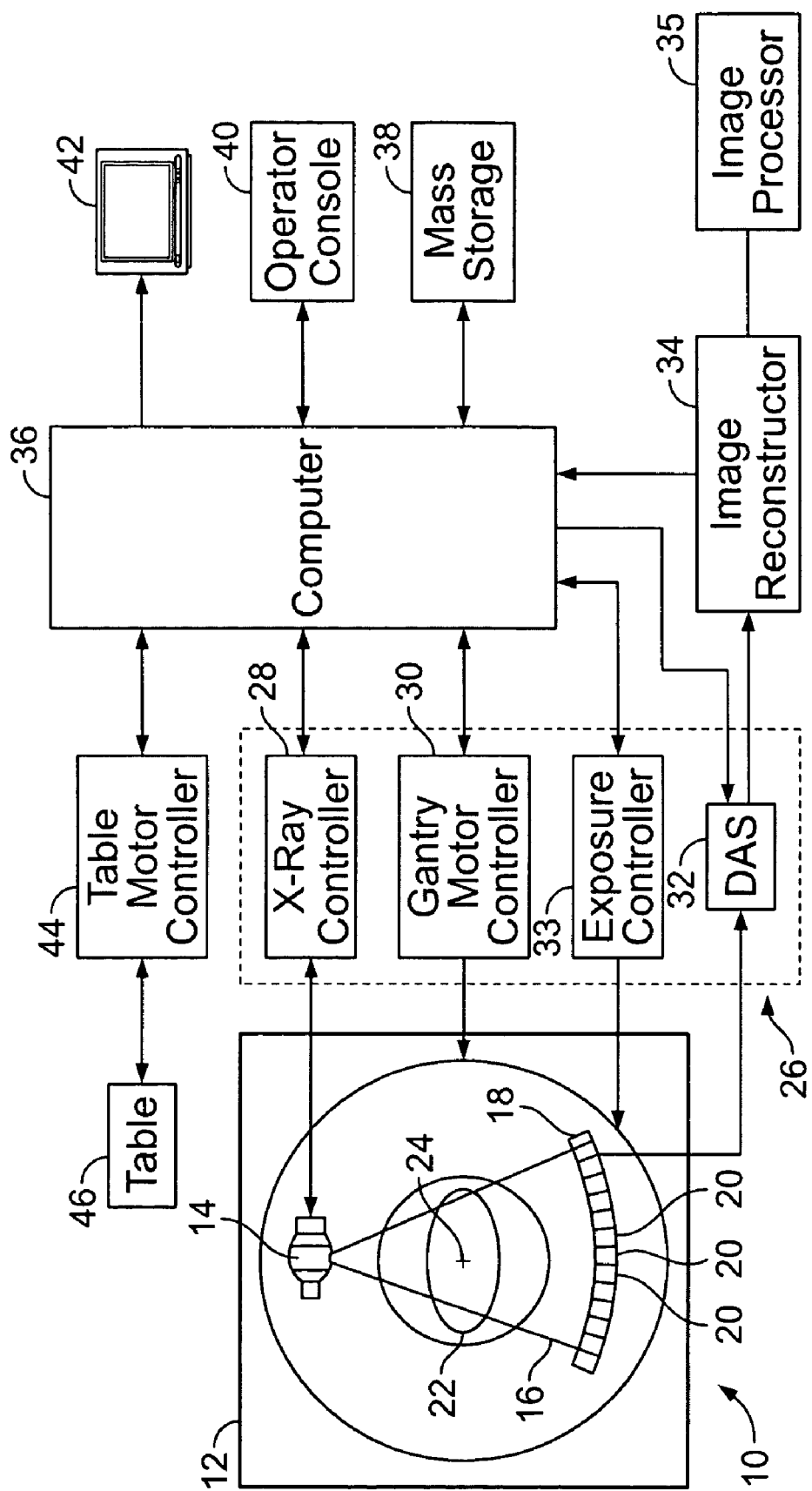
FIG. 1 is a block diagram of an X-ray imaging system in accordance with an exemplary embodiment of the present invention.

FIG. 1 illustrates a block diagram of an exemplary embodiment of an X-ray imaging system 10. The X-ray imaging system 10 includes a gantry 12 or other support structure having an X-ray source 14 that projects X-rays 16 (e.g., a beam of X-rays) toward a detector unit, such as a detector array 18 or other image receptor, which may be located on the opposite side of the gantry 12. The detector array 18 may be formed by a plurality of detector elements 20, which together detect the projected X-rays that pass through an object, such as a patient 22. Each of the plurality of detector elements 20 produces an electrical signal that represents the intensity of an impinging X-ray beam and hence the attenuation of the beam as it passes through the patient 22. During a scan to acquire X-ray projection data, and in various embodiments of the present invention, the gantry 12 and the components mounted thereon may rotate above a center of rotation 24. However, other movement is possible depending upon the type of X-ray scanner. Further, it should be noted that although the plurality of detector elements 20 are shown arranged in one row, different configurations are contemplated based upon the type of application and/or X-ray scanner used. The single row arrangement of the plurality of detector elements 20 allows projection data corresponding to a single image slice to be acquired during a scan. However, in other exemplary embodiments, the plurality of detector elements 20 may be arranged in a plurality of parallel rows such that projection data corresponding to a plurality of parallel slices can be acquired simultaneously during a scan.

Control of the gantry 12 such as, for example, rotation thereof, and the operation of the X-ray source 14 are provided by a control unit 26 of the X-ray imaging system 10. The control unit 26 includes an X-ray controller 28 that provides power and timing signals to the X-ray source 14 and a gantry motor controller 30 that controls, for example, the rotational speed and position of the gantry 12. A data acquisition system (DAS) 32 in the control unit 26 samples data, such as analog data, from the plurality of detector elements 20 and converts the data to digital signals for subsequent processing. The control unit 26 also includes an exposure controller 33 that controls the exposure level, such as the energy level of the X-ray source 14 and as described in more detail herein. An image reconstructor 34 receives sampled and digitized X-ray data from DAS 32 and performs image reconstruction. An image processor 35 also may be provided to process the X-ray data. The reconstructed image is provided to a processor, such as a computer 36 that stores the image in a storage device, such as a mass storage device 38 (e.g., disk storage).

Figure 2:
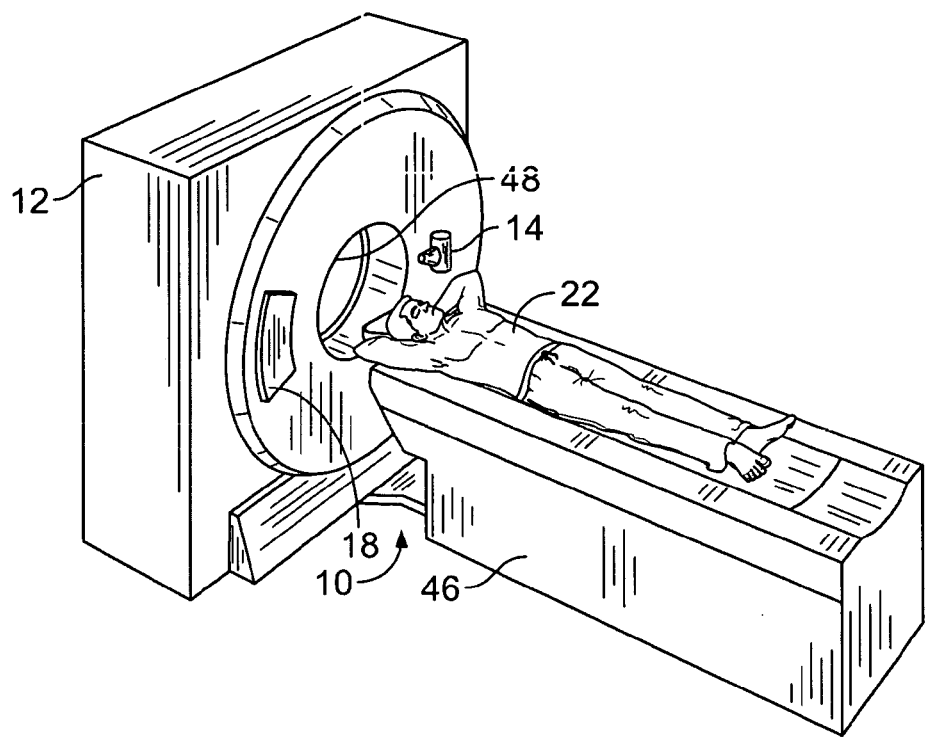
FIG. 2 is a perspective view of an exemplary embodiment of the X-ray imaging system of FIG. 1 shown as a computed tomography (CT) imaging system.
Figure 3:
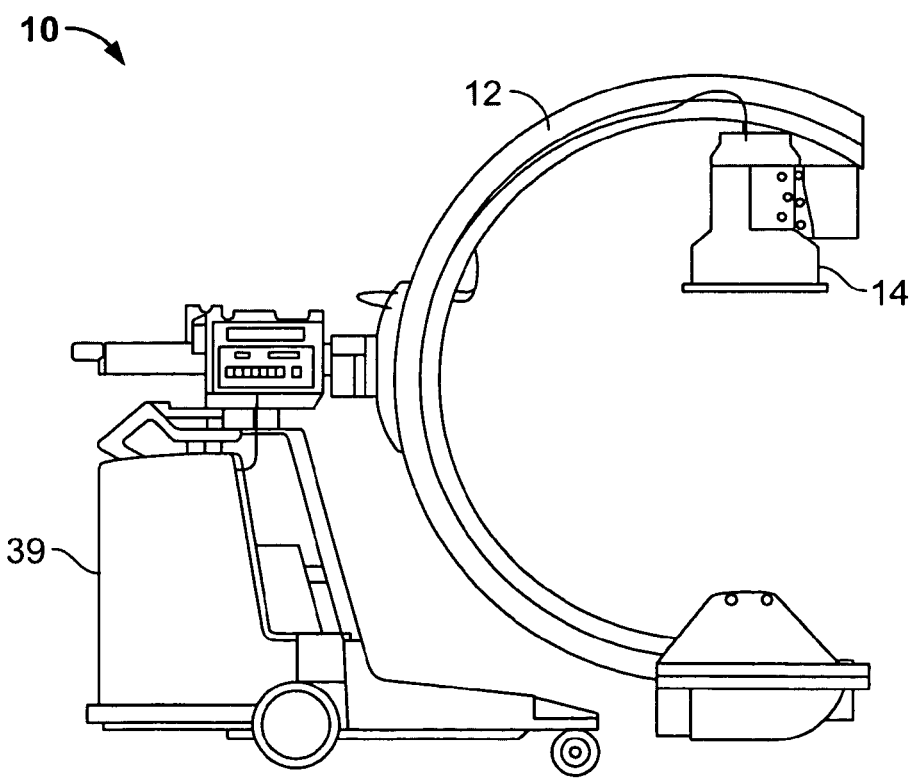
FIG. 3 is a side elevation view of another exemplary embodiment of the X-ray imaging system of FIG. 1 shown as a mobile C-arm X-ray system.
Figure 4:
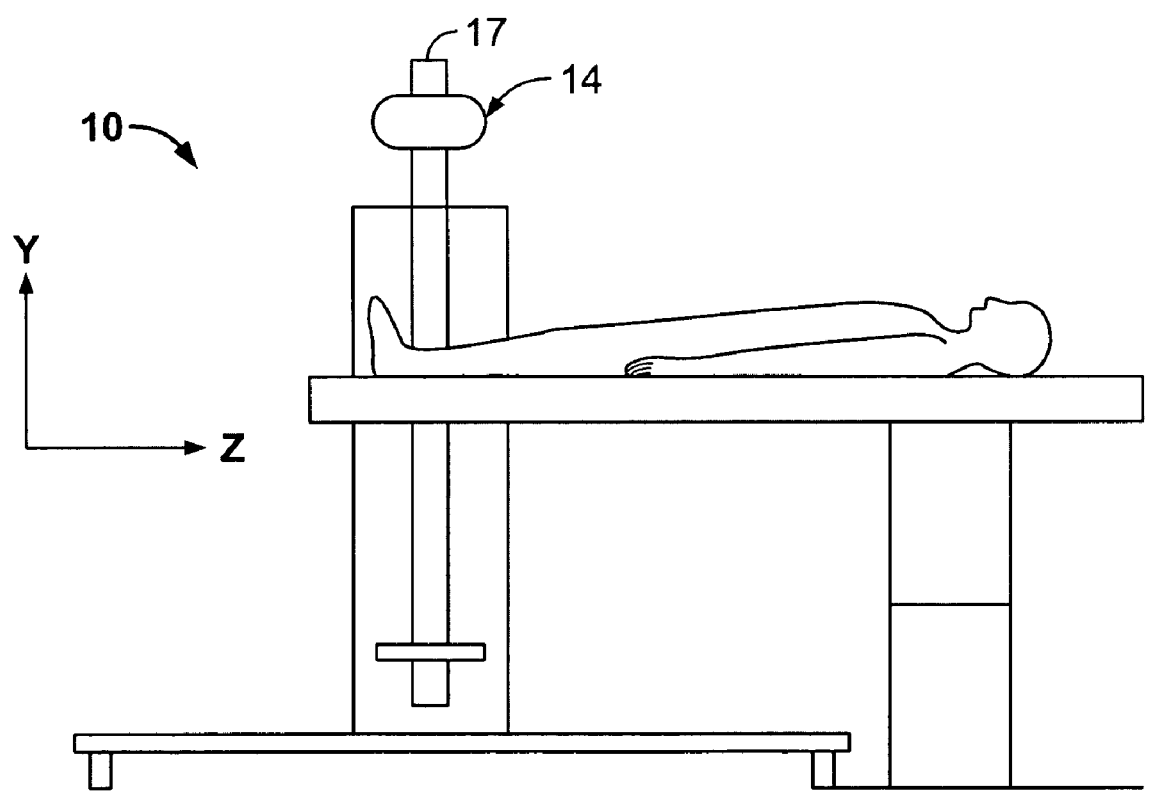
FIG. 4 is a side elevation view of another exemplary embodiment of the X-ray imaging system of FIG. 1 shown as a mobile X-ray imaging system.

The computer 36 also receives commands and scanning parameters from an operator via an operator console 40, which may include, for example, a keyboard, joystick, roller ball or other user input. A display 42 allows the operator to view the reconstructed image and other data from the computer 36. The operator supplied commands and parameters are used by the computer 36 to provide control signals and information to the DAS 32, X-ray controller 28, gantry motor controller 30 and exposure controller 33. In addition, and in one exemplary embodiment, the computer 36 controls a table motor controller 44 that controls a motorized table 46 to position a patient 22 in the gantry 12. For example, and as shown in FIG. 2, illustrating one embodiment of an X-ray medical imaging system 10 shown as a computed tomography (CT) imaging system, the table 46 moves portions of the patient 22 through a gantry opening 48. However, it should be noted that various embodiments of the present invention are not limited to the CT X-ray system shown in FIG. 2. For example, the X-ray imaging system 10 may be a mobile C-arm X-ray imaging system as shown in FIG. 3 having a C-shaped gantry 12 with the control components described in FIG. 1 provided as part of a mobile base 39. As another example and in another embodiment of the present invention as shown in FIG. 4, the X-ray imaging system 10 may be a mobile X-ray imaging system having a positioning arm 17 for moving the X-ray source 14. It should be noted, however, that the control components of the X-ray imaging system 10, including the exposure controller 33 (shown in FIG. 1) and image processor 35 (shown in FIG. 1) as described in more detail herein may be provided in connection with any type of X-ray imaging system as desired or needed.

Figure 5:
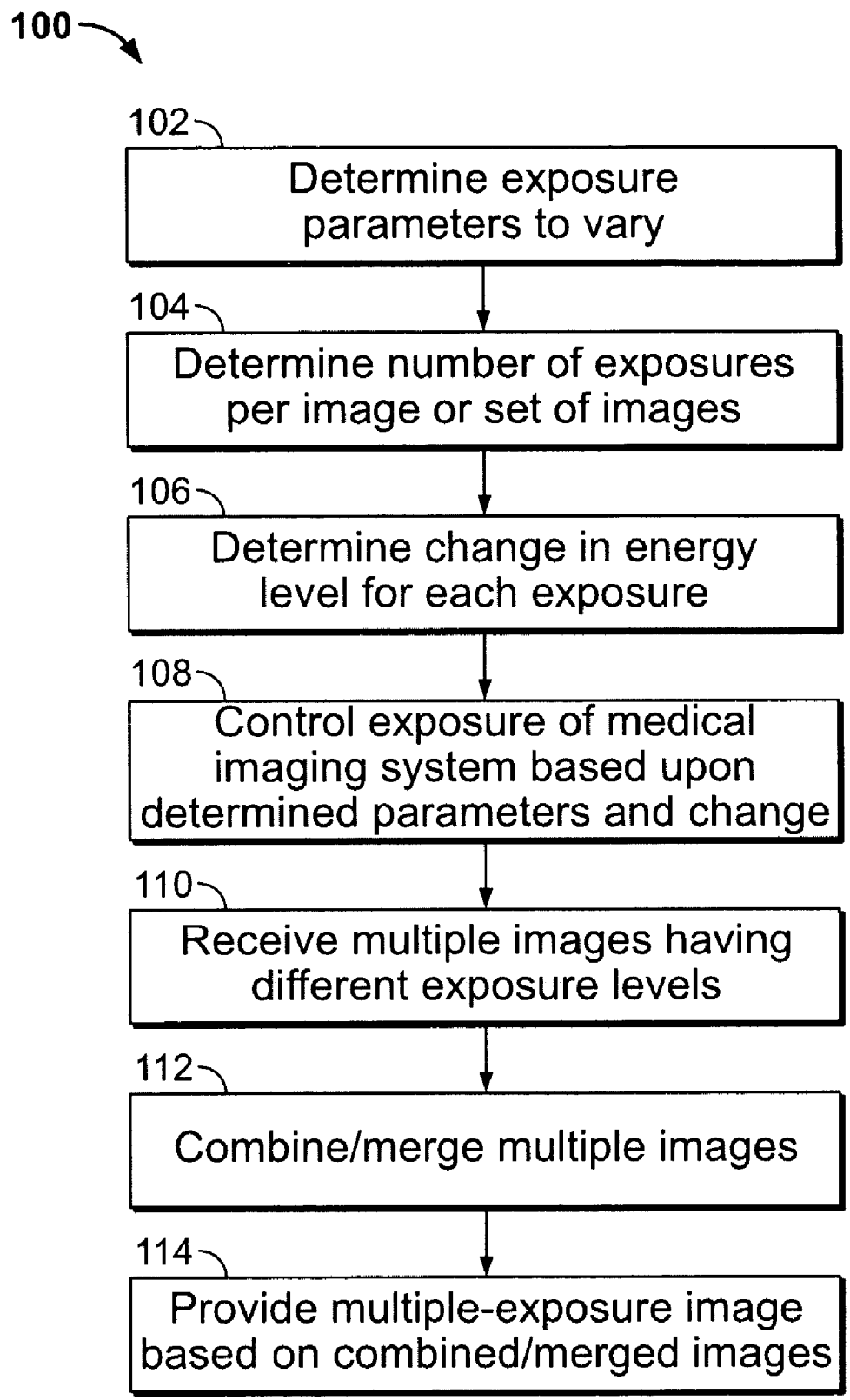
FIG. 5 is a flow chart illustrating an exposure control process in accordance with an exemplary embodiment of the present invention.

Various embodiments of the present invention allow for control of an X-ray imaging system 10, and more particularly, allow control of the exposure of images. The various embodiments are particularly useful for lower cost image sensors, such as image intensifiers, and improves the dynamic range of these detectors. Specifically, and as shown in FIG. 5, an exposure control process or method 100 for use in the X-ray system 10 is illustrated. In particular, at 102 a determination is made as to the exposure parameters to vary. In various embodiments these parameters generally include, but are not limited to, energy parameters, such as, for example: (i) the duration of the X-rays, which may be electronically controlled by varying the pulse width or mechanically controlled by a mechanical shutter; (ii) milliamp (mA) level, (iii) kilovolt (kV) level and/or (iv) other parameter that varies the X-ray dose applied by the X-ray imaging system 10, and in particular by the X-ray source 14, to provide variable sensor brightness. It should be noted that when reference is made herein to mAs this refers to the mA level over a duration of time. These parameters may be entered by a user using the operator console 40 (shown in FIG. 1) or may be predetermined and programmed for processing by the computer 36 (shown in FIG. 1), for example, based upon a particular type of examination to be performed.

At 104 a determination is made as to the number of exposures per image or set of images. Specifically, a determination is made as to the number of exposures at each position or point of the X-ray source 14 (shown in FIG. 1). For example, a dual exposure (i.e. two exposures using the x-ray source 14) may be provided at each location. However, additional exposures may be provided, including more than two and/or as many as needed or desired. At 106 a determination is made as to the desired or needed change in exposure level, for example the change in energy level, between each exposure per image or set of images. For example, the energy level may be changed based on a desired image quality selected by a user. The determination of the number of exposures per image or set of images at 104 and the determination of the change in exposure level for each exposure at 106 may again be based upon a user input received at the operator console 40 or may be predetermined.

At 108 the X-ray dose or exposure level of the X-rays 16 (shown in FIG. 1) generated by the X-ray source 14 are controlled (e.g., varied) by the exposure controller 33 (shown in FIG. 1) based upon the exposure parameters to be varied as determined at 102, the number of exposures per image or set of images as determined at 104 and the change in exposure level for each exposure as determined at 106. For example, the kV or mAs of the X-ray source 14 is controlled, and more specifically, varied for each of the exposures that is controlled by the exposure controller 33.

At 110 multiple images having different exposure levels are received. For example, the DAS 32 (shown in FIG. 1) samples analog data from the detector from the plurality of detector elements 20 (shown in FIG. 1) and then may convert the data to digital signals for subsequent processing. The sampling of data from the plurality of detector elements 20 may occur, for example, sequentially for each exposure level per image or set of images. The received multiple images are then combined or merged at 112. Specifically, the image processor 35 (shown in FIG. 1) in connection with the image reconstructor 34 (shown in FIG. 1) combines or merges the multiple images, for example, combines or merges multiple images at different exposure levels from the same point or position of the X-ray source 14 (shown in FIG. 1).

In operation, and for example, if two different exposure levels are provided (e.g., generated) by the X-ray source 14 for each image or set of images, then, for example, a dual energy combination or merging may be provided. In an exemplary embodiment, an additive and/or averaging merge or combination as is known is provided For example, a summation equation as is known may be used wherein the values of each pixel of the image are the summation of the Log of the pixel of the multiple images. However, it should be noted that any suitable method or process for combining or merging the images may be implemented. For example, any method or process as desired or needed may be used to combine or merge the images to avoid dark and/or bright clipping to provide an image having improved dynamic range. It further should be noted that in one exemplary embodiment the multiple images at each location are obtained while the X-ray source 14 and patient 22 (shown in FIG. 1) are stationary. The combined and/or merged images are then provided as a multiple-exposure image at 114, which may be displayed, for example on the display 42 (shown in FIG. 1).

Thus, various embodiments of the present invention provide multiple-exposure images from an X-ray scan. For example, multiple images with each exposure having a different energy level that are combined or merged to generate a multiple-exposure image having improved dynamic range and reduced dark/bright clipping using a lower cost sensor such as an image intensifier is provided. The multiple images may be combined in any manner such as additive, simple averaging, or other complex merger that reduces, for example, dark and/or bright clipping to improve the dynamic range of the images. Thus, and for example, multiple-exposure images generated by combining or merging multiple images with different exposures may be provided that extend the dynamic range of imagery construction using an X-ray system.

Further, it should be noted that the various embodiments of the present invention for providing exposure control may be used in connection or in combination with any type or kind of X-ray imaging system as desired or needed. Further, the parameters varied may be changed or modified, for example, based upon the type or kind of X-ray system or the particular X-ray application.

While the invention has been described in terms of various specific embodiments, those skilled in the art will recognize that the invention can be practiced with modification within the spirit and scope of the claims.

What is claimed is:

1. A method for controlling an X-ray imaging system, said method comprising:

determining exposure parameters to control to vary an exposure level of X-rays within an X-ray imaging system;

determining a number of exposures at each position of an X-ray source of the X-ray imaging system;

varying the exposure level of X-rays within the X-ray imaging system based on the determined exposure parameters and the determined number of exposures to generate a plurality of images for each position of the X-ray source and having different exposure levels; and combining the plurality of images in an additive process to form a single X-ray image.

2. A method in accordance with claim 1 wherein varying the exposure level comprises varying an X-ray dose.

3. A method in accordance with claim 1 wherein varying the exposure level comprises varying an energy level of the X-rays.

4. A method in accordance with claim 3 wherein varying the energy level comprises varying one of duration, milliamp level and kilovolt level.

5. A method in accordance with claim 3 wherein varying the energy level comprises varying a milliamp per second (mAs) level.

6. A method in accordance with claim 1 wherein varying the exposure level comprises varying an energy level of the X-rays, the energy level comprising one of duration, milliamp level and kilovolt level, and the duration controlled by one of electronic and mechanical means.

7. A method in accordance with claim 1 wherein the additive process comprises an averaging process.

8. A method in accordance with claim 1 further comprising acquiring the plurality of images at a single position of the X-ray system.

9. A method in accordance with claim 1 further comprising acquiring a plurality of images at each of a plurality of positions of the X-ray system.

10. A method in accordance with claim 1 further comprising determining parameters to be varied for use in varying the exposure level based upon a user input.

11. A method in accordance with claim 1 further comprising determining the change in exposure level to be varied based upon a user input.

12. A method in accordance with claim 1 further comprising minimizing one of dark and light clipping when combining the plurality of images.

13. A method in accordance with claim 1 wherein the single X-ray image comprises a multiple-exposure image.

14. A method for generating an X-ray image, said method comprising:

determining exposure parameters to control to vary an exposure level;

determining a number of exposures for each of a plurality of positions of an X-ray imaging system;

receiving a plurality of images corresponding to the plurality of exposures, each having a different exposure level varied based on the determined exposure parameters and the number of exposures; and combining in an additive process the plurality of images to generate a single X-ray image.

15. A method in accordance with claim 14 wherein each of the plurality of images are generated at a different energy level.

16. A method in accordance with claim 14 wherein each of the plurality of images are generated relative to a single position of an X-ray imaging device.

17. A method in accordance with claim 14 further comprising minimizing one of dark and light clipping when combining the plurality of images.

18. A method in accordance with claim 14 further comprising increasing dynamic range when combining the plurality of images.

19. A method in accordance with claim 14 further comprising receiving user inputs to define the exposure levels.

20. An X-ray system comprising:

an X-ray imaging device for acquiring X-ray images;

a controller for controlling selected exposure parameters to vary an exposure level of a plurality of images acquired at each of a plurality of positions of the X-ray imaging device, and for controlling a number of exposures at each of the plurality of positions defining the plurality of images; and a processor for processing a plurality of acquired images each having a different exposure level in order to combine in an additive process the plurality of acquired images to generate a single X-ray image.

* * * * *